US012680070B2

(12) United States Patent
Feng et al.

(10) Patent No.: US 12,680,070 B2
(45) Date of Patent: Jul. 14, 2026

(54) DEVICE AND METHOD FOR SINGLE-CELL HIGH-THROUGHPUT SORTING IN MARINE IN-SITU ENVIRONMENT

(71) Applicants: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

(72) Inventors: Jingchun Feng, Guangdong (CN); Si Zhang, Guangdong (CN); Zhifeng Yang, Guangdong (CN); Yi Wang, Guangdong (CN); Yanpeng Cai, Guangdong (CN); Song Zhong, Guangdong (CN)

(73) Assignees: GUANGDONG LABORATORY OF SOUTHERN OCEAN SCIENCE AND ENGINEERING (GUANGZHOU), Guangdong (CN); GUANGDONG UNIVERSITY OF TECHNOLOGY, Guangdong (CN)

( * ) Notice: Subject to any disclaimer, the term of this patent is extended or adjusted under 35 U.S.C. 154(b) by 687 days.

(21) Appl. No.: 18/019,790

(22) PCT Filed: Mar. 30, 2022

(86) PCT No.: PCT/CN2022/083914
§ 371 (c)(1),
(2) Date: Feb. 3, 2023

(87) PCT Pub. No.: WO2023/173486
PCT Pub. Date: Sep. 21, 2023

(65) Prior Publication Data
US 2024/0052290 A1 Feb. 15, 2024

(30) Foreign Application Priority Data

Mar. 15, 2022 (CN) .......................... 202210251474.8

(51) Int. Cl.
*C12M 1/00* (2006.01)
*C12M 1/34* (2006.01)
(52) U.S. Cl.
CPC ............ *C12M 47/04* (2013.01); *C12M 41/12* (2013.01); *C12M 41/40* (2013.01)
(58) Field of Classification Search
CPC ....... C12M 47/04; C12M 41/12; C12M 41/40
(Continued)

(56) References Cited

U.S. PATENT DOCUMENTS

2012/0122084 A1 5/2012 Wagner et al.

FOREIGN PATENT DOCUMENTS

CN 105588827 5/2016
CN 111239132 A * 6/2020 ............. G01N 21/84
(Continued)

OTHER PUBLICATIONS

CN113818843A Machine English Translation (Year: 2021).*
(Continued)

*Primary Examiner* — Michael L Hobbs
*Assistant Examiner* — Lenora A Abel
(74) *Attorney, Agent, or Firm* — JCIPRNET

(57) ABSTRACT

The present invention provides a device for single-cell high-throughput sorting in a marine in-situ environment. The device includes a pressure-resistant visual sorting cabin, an optical identification system and an automatic sorting system; a microorganism-containing bacteria liquid is injected into the pressure-resistant visual sorting cabin; the enriched microorganisms is dispersed and pass through a channel via a carrier chip disposed in the pressure-resistant
(Continued)

visual sorting cabin; when the enriched microorganisms pass through the carrier chip, the microorganisms are observed and identified via the optical identification system; and the automatic sorting system automatically sorts the microorganisms according to a microorganism identification result. The present invention further provides a method for single-cell high-throughput sorting in the marine in-situ environment. After single-cell dispersion of the microorganisms is achieved through the carrier chip, the microorganisms are observed and identified via the optical identification system, and sorted through the automatic sorting system intelligently.

17 Claims, 3 Drawing Sheets

(58) Field of Classification Search
USPC ....................................................... 435/308.1
See application file for complete search history.

(56) References Cited

FOREIGN PATENT DOCUMENTS

| CN | 111477084 | | | 7/2020 | | |
|----|-----------|---|---|--------|---|---|
| CN | 111477084 | A | * | 7/2020 | ............. | G09B 23/40 |
| CN | 111500440 | | | 8/2020 | | |
| CN | 113136324 | | | 7/2021 | | |
| CN | 113477282 | | | 10/2021 | | |
| CN | 113818843 | | | 12/2021 | | |
| CN | 113818843 | A | * | 12/2021 | ............. | E21B 47/00 |

OTHER PUBLICATIONS

CN-111239132-A Machine English Translation (Year: 2020).*
CN-111477084-B Machine English Translation (Year: 2020).*
"International Search Report (Form PCT/ISA/210) of PCT/CN2022/083914", mailed on Nov. 25, 2022, pp. 1-5.
Zhou Jing et al., "Diversity of Extremophilic Miroorganisms and Their Applications", Journal of Glaciology and Geocryology, vol. 29, Issue 2, Apr. 2007, with English abstract, pp. 286-291.

* cited by examiner

DEVICE AND METHOD FOR SINGLE-CELL HIGH-THROUGHPUT SORTING IN MARINE IN-SITU ENVIRONMENT

CROSS-REFERENCE TO RELATED APPLICATION

This is a 371 application of the International PCT application serial no. PCT/CN2022/083914, filed on Mar. 30, 2022, which claims the priority benefits of China Application No. 202210251474.8, filed on Mar. 15, 2022. The entirety of each of the above-mentioned patent applications is hereby incorporated by reference herein and made a part of this specification.

TECHNICAL FIELD

The present invention relates to the technical field of marine microorganisms, in particular to a device and method for single-cell high-throughput sorting in a marine in-situ environment.

DESCRIPTION OF RELATED ART

As the cradle of life on earth, the vast ocean contains rich resources and a wide variety of microorganisms. Marine microorganisms are important marine biological resources. Metabolites of marine bacteria, marine fungi, marine actinomycetes and marine archaea inside sea water and marine sediments have a large number of bioactive substances, which have important application prospects in the fields of energy, materials, environment, medicine, etc. For example, autotrophic microorganisms capable of producing bioenergy are found in deep-sea cold seeps and hydrothermal environments; marine microorganisms capable of degrading plastics have been discovered; scientists have isolated effective antibiotics from marine bacteria and actinomycetes; and marine archaea such as methanotrophs have strong methane metabolism capacity, and as primary producers of extreme marine ecosystems, they are symbiotic with metazoa through chemoenergetic synthesis, providing the metazoa with an important source of carbon and energy. Therefore, marine microorganisms are important biological resources with significant exploitation value.

Isolation and culture are important prerequisites for the development and utilization of marine microorganisms. At present, the isolation of marine microorganisms is mostly carried out by plate streaking under atmospheric pressure or using a single cell sorter, but the marine microorganisms that have been isolated are still less than 1%. The mechanisms and characteristics of microorganisms such as physiology, biogeochemistry and ecology are not easy to obtain directly from nature, so it is an important basis to isolate microorganisms from natural environment and establish pure culture for studying their gene sequence, morphological characteristics, physiological characteristics and ecological characteristics. However, marine microorganisms mostly live in extreme environments, for example, piezophilic microorganisms can hardly be isolated and cultured in an atmospheric pressure environment, which limits our understanding on marine microorganisms and their value in exploitation and utilization. Therefore, there is an urgent need to develop effective identification and sorting techniques for microorganisms in marine high-pressure environments.

A method for detecting aerobic anoxygenic phototrophic bacteria based on single-cell Raman spectroscopy is disclosed in the prior art, which achieves single-cell detection of aerobic non-oxygenic photosynthetic bacteria in environmental water. Detection by Raman spectroscopy is non-destructive, and the detected aerobic anoxygenic phototrophic bacteria may be used for single-cell sorting and sequencing. However, due to the special environment in which deep-sea microorganisms live, the above solution is not applicable to the identification and sorting of deep-sea microorganisms.

SUMMARY

In order to overcome at least one of the above-mentioned technical defects, the present invention provides a device and method for single-cell high-throughput sorting in a marine in-situ environment, which achieves high-throughput single-cell identification and sorting of marine microorganisms through optical and spectral detection in a high-pressure environment, improving culturability of the marine microorganisms.

In order to solve the above-mentioned technical problems, the present invention adopts the following technical solutions.

A device for single-cell high-throughput sorting in a marine in-situ environment includes an enriched microorganism injection system, a pressure-resistant visual sorting cabin, an annular wall temperature controlling system, a pressurization system, an annular pressure controlling system, an optical identification system, an automatic sorting system, and a data acquisition and processing system. The enriched microorganism injection system is used for culturing and injecting a microorganism-containing bacteria liquid into the pressure-resistant visual sorting cabin. A carrier chip is disposed in the pressure-resistant visual sorting cabin, the carrier chip is made of visual material and embedded with an etching microfluidic channel for allowing the enriched microorganisms to be dispersed and to pass through the channel; when the enriched microorganisms pass through the carrier chip, the microorganisms are observed and identified via the optical identification system; an outlet end of the pressure-resistant visual sorting cabin is connected to the automatic sorting system, and the automatic sorting system automatically sorts the microorganisms according to a microorganism identification result of the optical identification system; the annular wall temperature controlling system is used for ensuring consistent internal temperature of the pressure-resistant visual sorting cabin; the pressurization system is used for meeting the function requirement for consistency between internal pressure of the pressure-resistant visual sorting cabin and internal pressure of the enriched microorganism injection system; the annular pressure controlling system is used for keeping the internal pressure of the pressure-resistant visual sorting cabin consistent with internal pressure of the automatic sorting system according to a pressure value change therein, so as to avoid deformation or damage to the carrier chip from a pressure difference; and the enriched microorganism injection system, the annular wall temperature controlling system, the pressurization system, the annular pressure controlling system, the optical identification system, and the automatic sorting system are all electrically connected to the data acquisition and processing system.

In the above-mentioned solution, the carrier chip is provided with microtine inlet and outlet channels, and the inlet channel is mainly used for pumping the microorganism-containing bacteria liquid from the enriched microorganism injection system, and injecting gas and liquid from the pressurization system for pressurization.

In the above-mentioned solution, the carrier chip is provided to allow the microorganisms to be dispersed and to pass, and the microorganisms are observed and identified via the optical identification system. Then sorted through the automatic sorting system intelligently, such that a high-throughput single-cell identification and sorting process of marine microorganisms by optical and spectral detection in the high-pressure environment is achieved, and culturability of the marine microorganisms is effectively improved.

This solution provides the device and technology for high-throughput single-cell sorting in the high-pressure environment to address the current challenge that marine microorganisms are difficult to isolate. Compared with the existing atmospheric pressure isolation and culture, enrichment and isolation of microorganisms in the deep-sea in-situ high-pressure environment can be realized, and the problem that deep-sea in-situ piezophilic bacteria cannot survive or express differently when cultured in an atmospheric pressure environment can be solved. On the other hand, this solution provides an idea and method for high-throughput sorting of microorganisms according to specific morphological and metabolic characteristics. Compared with conventional enrichment and plate streaking isolation technology, the present solution can solve the problem of difficulty in enrichment, isolation and culture of marine high-pressure environmental microorganisms out of the high-pressure environment, and can also achieve high-throughput identification and sorting of marine microorganisms at single-cell scale under a high-pressure condition, and improve the isolation efficiency.

Particularly, the enriched microorganism injection system includes a microflow pump, a high-pressure microorganism enrichment and culturing chamber, and an inlet pressure detection device. A control end of the microflow pump is electrically connected to the data acquisition and processing system; an input end of the microflow pump is connected to a liquid outlet end of the high-pressure microorganism enrichment and culturing chamber, and an output end of the microflow pump is connected to an inlet end of the pressure-resistant visual sorting cabin through the inlet pressure detection device. The high-pressure microorganism enrichment and culturing chamber is used for culturing the microorganism-containing bacteria liquid and injecting the microorganism-containing bacteria liquid into the pressure-resistant visual sorting cabin via the microflow pump.

Particularly, the pressure-resistant visual sorting cabin further includes a pressure-resistant visual cavity, an annular wall refrigerating/heating cavity, and an annular wall high-pressure cavity; the pressure-resistant visual cavity is made of pressure-resistant and anti-corrosion metal material, pressure-resistant visual material is inlaid on a front side and a back side of the pressure-resistant visual cavity, and the whole pressure-resistant visual cavity may bear pressure at a water depth of 5000 meters, and is connected to the pressurization system; the carrier chip is disposed in a center of the pressure-resistant visual cavity; an inlet of the microfluidic channel of the carrier chip is connected to the enriched microorganism injection system, and an outlet of the microfluidic channel is the outlet end of the pressure-resistant visual sorting cabin, and is connected to the automatic sorting system; the annular wall high-pressure cavity is disposed at an outer ring of the pressure-resistant visual cavity for protecting the carrier chip against damage in the pressure-resistant visual cavity; the annular wall high-pressure cavity is connected to the pressurization system and the annular pressure controlling system; and the annular wall refrigerating/heating cavity is wrapped on an outer wall of the pressure-resistant visual cavity for loading a refrigerating/heating fluid, and is connected to the annular wall temperature controlling system through the refrigerating/heating fluid.

In the above-mentioned solution, the pressure-resistant visual cavity is provided with a discharge valve, and an output end of the discharge valve is electrically connected to the data acquisition and processing system to facilitate pressure regulation in the cavity. In order to protect the carrier chip against damage in the pressure-resistant visual cavity, the pressure-resistant visual cavity is provided with the annular wall high-pressure cavity for pressurization at the outer ring of the pressure-resistant visual cavity at the same time. In addition, the annular pressure controlling system is provided to automatically increase or decrease pressure of the annular wall high-pressure cavity according to a pressure change of the pressure-resistant visual cavity, so as to achieve pressure balance between the pressure-resistant visual cavity and the annular wall high-pressure cavity and ensure that the carrier chip is subjected to the minimum pressure difference without damage.

Particularly, the annular wall temperature controlling system adopts a circulating refrigerating/heating device and a temperature sensor. A control end of the circulating refrigerating/heating device is electrically connected to the data acquisition and processing system for refrigerating/heating and enabling the refrigerating/heating fluid in the annular wall refrigerating/heating cavity to flow circularly. A probe of the temperature sensor is disposed in the pressure-resistant visual cavity, and a signal output end of the temperature sensor is electrically connected to the data acquisition and processing system.

In the above-mentioned solution, the temperature of the pressure-resistant visual cavity is ensured mainly by injecting the refrigerating/heating fluid in the annular wall refrigerating/heating cavity, a low or high temperature state of the fluid in the annular wall refrigerating/heating cavity is ensured by refrigerating or heating the fluid circularly, and a low or high temperature state in the pressure-resistant visual cavity is ensured through heat exchange between the refrigerating/heating fluid and the pressure-resistant visual cavity.

Particularly, the pressurization system includes an air compressor, a booster pump, a gas storage tank, a pressure regulating valve, and a pressure sensor; the air compressor, the booster pump, the gas storage tank, and the pressure regulating valve are connected in sequence, and then are connected to the pressure-resistant visual cavity and the annular wall high-pressure cavity, respectively; and a probe of the pressure sensor is disposed in the pressure-resistant visual cavity, and a signal output end of the pressure sensor is electrically connected to the data acquisition and processing system.

In the above-mentioned solution, the temperature sensor and the pressure sensor are provided to measure and monitor the temperature and pressure of the pressure-resistant visual cavity in the whole microorganism sorting process.

Particularly, the annular pressure controlling system includes an annular pressure detection device, a first back pressure tracking pump, a back pressure detection device, a back pressure valve, a buffer tank, and a second back pressure tracking pump; a probe of the annular pressure detection device is disposed in the annular wall high-pressure cavity, and an output end of the annular pressure detection device is electrically connected to the data acquisition and processing system; the first back pressure tracking pump is connected to the annular wall high-pressure cavity, and a control end of the first back pressure tracking pump is electrically connected to the data acquisition and processing system; a detection end of the back pressure detection device is connected to the pressure-resistant visual cavity, and a signal output end of the back pressure detection device is electrically connected to the data acquisition and processing system; one end of the back pressure valve is connected to the automatic sorting system, and the other end of the back pressure valve is connected to the second back pressure tracking pump through the buffer tank; and a control end of the second back pressure tracking pump is electrically connected to the data acquisition and processing system.

Particularly, the optical identification system adopts a spectral/optical observation module, observes and identifies the microorganisms via the spectral/optical observation module when the enriched microorganisms pass through the carrier chip, and sends the identification result to the data acquisition and processing system.

In the process that the enriched microorganisms pass through the carrier chip, the microorganisms are observed and identified via the spectral/optical observation module. The morphology of single cells may be identified by looking over the chip with a high resolution optical microscope, marker biological compounds in the cells may be identified by Raman spectroscopy, and whether microorganisms in the chip are target microorganisms needed by researchers may be determined in combination with optical and spectroscopy identification signals.

Particularly, the automatic sorting system includes an intelligent control tee module, a target microorganism storage module and a non-target microorganism storage module; the target microorganism storage module and the non-target microorganism storage module are connected to two connecting ends of the intelligent control tee module respectively, and another connecting end of the intelligent control tee module is connected to the outlet end of the pressure-resistant visual sorting cabin; and a control end of the intelligent control tee module is electrically connected to the data acquisition and processing system.

In the above-mentioned solution, the automatic sorting system is provided at the outlet end of the pressure-resistant visual cavity to perform targeted sorting on the identified microorganisms. The automatic sorting system is mainly controlled by the intelligent control tee module. The intelligent control tee module is an automatic opening and closing tee. When it is determined that identified single cells are target microorganisms, a valve of a channel of the non-target microorganism storage module is opened, and the single cells enter the non-target microorganism storage module. When it is determined that identified single cells are non-target microorganisms, a channel of the target microorganism storage module is opened, and the cells enter the target microorganism storage module. Thus, the purpose of high-throughput single-cell sorting is achieved. An atmospheric pressure container or a high pressure container may be selected as the target microorganism storage module according to experimental needs. The container contains a corresponding culture medium to meet the need of continuing to culture the sorted microorganisms.

This solution further provides a method for single-cell high-throughput sorting in a marine in-situ environment. The method is implemented by adopting a device for single-cell high-throughput sorting in the marine in-situ environment, and specifically includes the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of intracellular and extracellular metabolic compounds via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

Before step S1 is carried out, pretreatment needs to be carried out on the device for single-cell high-throughput sorting in the marine in-situ environment as follows: opening the outlet end of the pressure-resistant visual cavity, and repeatedly cleaning the pressure-resistant visual cavity by pumping in deionized water; after thorough rinsing, pumping in 75% alcohol; and after the pressure-resistant visual cavity is completely filled with alcohol, closing the pressure-resistant visual cavity, performing standing for 24 hours, and then discharging the alcohol in the pressure-resistant visual cavity to complete the pretreatment.

In the whole sorting process, the pressure and temperature values in the pressure-resistant visual cavity are kept consistent with the pressure and temperature environment in the enriched microorganism injection system where the microorganisms are initially located, such that the microorganisms are sorted under in-situ high-pressure conditions. In the sorting process, the annular pressure controlling system is started to keep the pressure value in the annular wall high-pressure cavity consistent with that in the pressure-resistant visual cavity according to a pressure value change therein, such that the carrier chip is not subjected to a pressure difference and is prevented from being deformed and damaged.

Through the chip and technology for high-throughput single-cell sorting of the marine microorganisms in the high-pressure environment provided in this solution, identification and sorting of the microorganisms in the marine high-pressure environment can be achieved, and the requirements of subsequent pure culture can be met. Compared with current traditional technology for enrichment and isolation of marine microorganisms in an atmospheric pressure environment, the problems that marine pressure-resistant bacteria and barophilic bacteria have a low survival rate in the atmospheric pressure environment, and deep-sea indigenous characteristics cannot be effectively expressed in the atmospheric pressure environment can be effectively solved, and the problems of low culture degree of marine microorganisms and difficulty in culturing pure bacteria at present are solved. Meanwhile, this solution can realize high-throughput identification and automatic sorting at single-cell scale in the high-pressure environment, which effectively improves the efficiency of microorganism culture and purification compared with conventional microorganism isolation and culture technology.

Compared with the prior art, the technical solution of the present invention has the following beneficial effects.

The present invention provides the device and method for single-cell high-throughput sorting in the marine in-situ environment. The carrier chip is provided to allow the microorganisms to be dispersed and to pass, and the microorganisms are observed and identified via the optical identification system, and then sorted through the automatic sorting system intelligently, such that a high-throughput single-cell identification and sorting process of the marine microorganisms by optical and spectral detection in the high-pressure environment is achieved, and the culturability of the marine microorganisms is effectively improved.

1 denotes an enriched microorganism injection system; 11 denotes a microflow pump; 12 denotes a high-pressure microorganism enrichment and culturing chamber; 13 denotes an inlet pressure detection device; 2 denotes a pressure-resistant visual sorting cabin; 21 denotes a carrier chip; 22 denotes an annular wall refrigerating/heating cavity; 23 denotes a discharge valve; 3 denotes an annular wall temperature controlling system; 31 denotes a circulating refrigerating/heating device; 32 denotes a temperature sensor; 4 denotes a pressurization system; 41 denotes an air compressor; 42 denotes a booster pump; 43 denotes a gas storage tank; 44 denotes a pressure regulating valve; 45 denotes a pressure sensor; 5 denotes an annular pressure controlling system; 51 denotes an annular pressure detection device; 52 denotes a first back pressure tracking pump; 53 denotes a back pressure detection device; 54 denotes a back pressure valve; 55 denotes a buffer tank; 56 denotes a second back pressure tracking pump; 6 denotes an optical identification system; 7 denotes an automatic sorting system; 71 denotes an intelligent control tee module; 72 denotes a target microorganism storage module; 73 denotes a non-target microorganism storage module; and 8 denotes a data acquisition and processing system.

DESCRIPTION OF THE EMBODIMENTS

The accompanying drawings are merely used for illustrating the present invention, and should not be construed as limitations on this patent.

The following examples are complete use examples with rich contents.

In order to better illustrate the examples, some parts in the accompanying drawings are omitted, enlarged, or reduced, and do not represent the size of actual products.

It may be understood by those skilled in the art that some well-known structures and descriptions thereof may be omitted from the accompanying drawings.

The technical solutions of the present invention are further described below in conjunction with the accompanying drawings and examples.

Example 1

Figure 1:
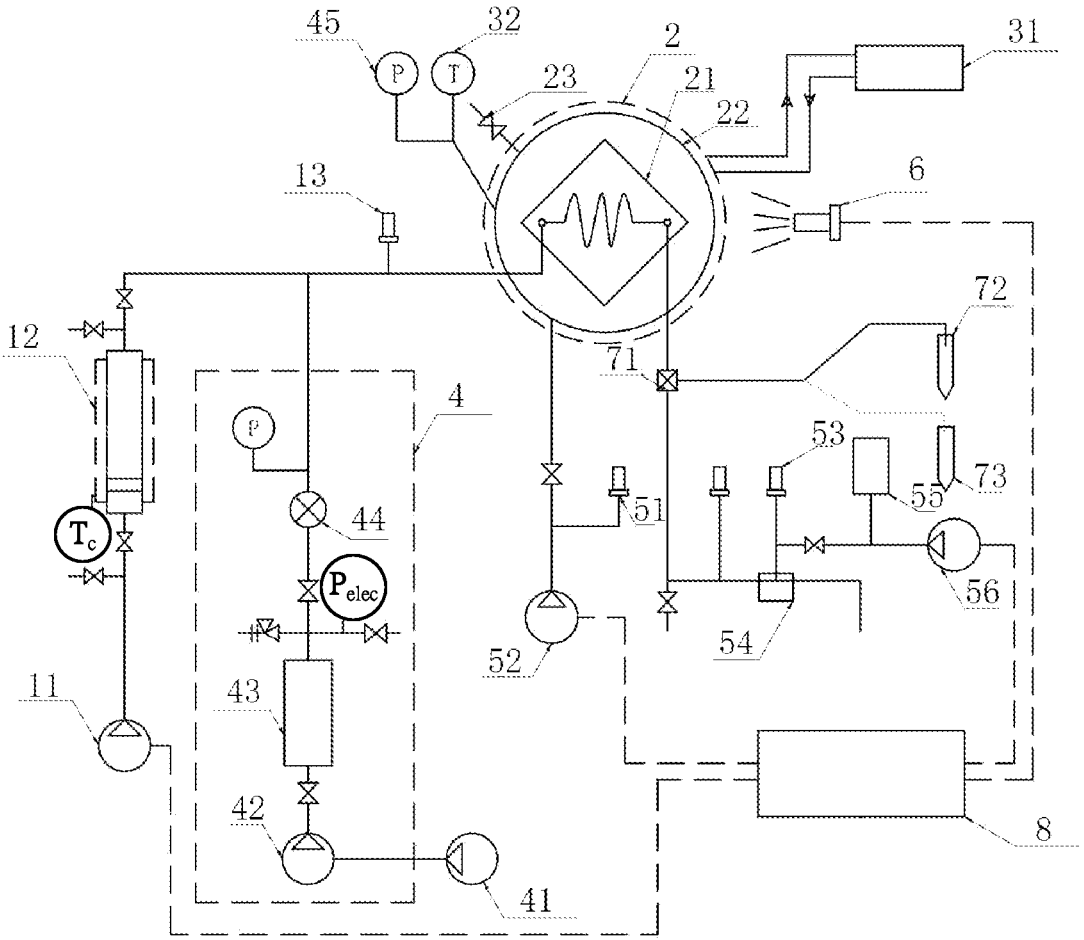
FIG. 1 is a schematic structural diagram of a device according to the present invention.
Figure 2:
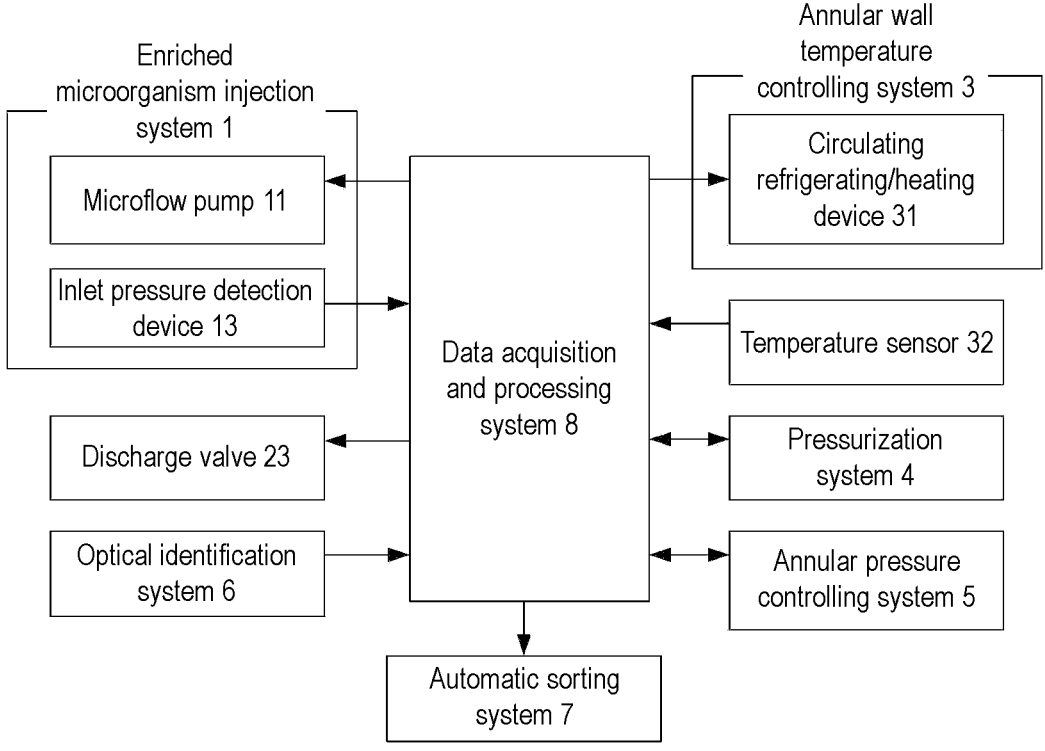
FIG. 2 is a schematic diagram of connection of circuit modules of a data acquisition and processing system according to the present invention.

As shown in FIG. 1 and FIG. 2, this example provides a device for single-cell high-throughput sorting in a marine in-situ environment. The device includes an enriched microorganism injection system 1, a pressure-resistant visual sorting cabin 2, an annular wall temperature controlling system 3, a pressurization system 4, an annular pressure controlling system 5, an optical identification system 6, an automatic sorting system 7, and a data acquisition and processing system 8. The enriched microorganism injection system 1 is used for culturing and injecting a microorganism-containing bacteria liquid into the pressure-resistant visual sorting cabin 2. A carrier chip 21 is disposed in the pressure-resistant visual sorting cabin 2. The carrier chip 21 is made of visual material and embedded with an etching microfluidic channel for allowing the enriched microorganisms to be dispersed and to pass through the channel. When the enriched microorganisms pass through the carrier chip 21, the microorganisms are observed and identified via the optical identification system 6. An outlet end of the pressure-resistant visual sorting cabin 2 is connected to the automatic sorting system 7, and the automatic sorting system 7 automatically sorts the microorganisms according to a microorganism identification result of the optical identification system 6. The annular wall temperature controlling system 3 is used for ensuring consistent internal temperature of the pressure-resistant visual sorting cabin 2. The pressurization system 4 is used for enabling internal pressure of the pressure-resistant visual sorting cabin 2 to be consistent with internal pressure of the enriched microorganism injection system 1. The annular pressure controlling system 5 is used for keeping the internal pressure of the pressure-resistant visual sorting cabin 2 consistent with internal pressure of the automatic sorting system 7 according to a pressure value change therein, so as to avoid deformation or damage to the carrier chip 21 from a pressure difference. The enriched microorganism injection system 1, the annular wall temperature controlling system 3, the pressurization system 4, the annular pressure controlling system 5, the optical identification system 6, and the automatic sorting system 7 are all electrically connected to the data acquisition and processing system 8.

In a specific implementation process, the carrier chip 21 is provided with microtine inlet and outlet channels, and the inlet channel is mainly used for pumping the microorganism-containing bacteria liquid from the enriched microorganism injection system 1, and injecting gas and liquid from the pressurization system 4 for pressurization.

In a specific implementation process, the carrier chip 21 is provided in this example to allow the microorganisms to be dispersed and to pass, the microorganisms are observed and identified via the optical identification system 6, and then sorted through the automatic sorting system 7 intelligently, such that a high-throughput single-cell identification and sorting process of marine microorganisms by optical and spectral detection in the high-pressure environment is achieved, and culturability of the marine microorganisms is effectively improved.

This example provides the device and technology for high-throughput single-cell sorting in the high-pressure environment to address the current challenge that marine microorganisms are difficult to isolate. Compared with existing atmospheric pressure isolation and culture, enrichment and isolation of microorganisms in the deep-sea in-situ high-pressure environment can be met, and the problem that deep-sea in-situ piezophilic bacteria cannot survive or express differently when cultured in the atmospheric pressure environment can be solved. On the other hand, this example provides an idea and method for high-throughput sorting of microorganisms according to specific morphological and metabolic characteristics. Compared with conventional enrichment and plate streaking isolation technology, the present example can solve the problem of difficulty in enrichment, isolation and culture of marine high-pressure environmental microorganisms out of the high-pressure environment, and can also achieve high-throughput identification and sorting of marine microorganisms at single-cell scale under a high-pressure condition, and improve the isolation efficiency.

More specifically, the enriched microorganism injection system 1 includes a microflow pump 11, a high-pressure microorganism enrichment and culturing chamber 12 and an inlet pressure detection device 13. A control end of the microflow pump 11 is electrically connected to the data acquisition and processing system 8. An input end of the microflow pump 11 is connected to a liquid outlet end of the high-pressure microorganism enrichment and culturing chamber 12, and an output end of the microflow pump is connected to an inlet end of the pressure-resistant visual sorting cabin 2 through the inlet pressure detection device 13. The high-pressure microorganism enrichment and culturing chamber 12 is used for culturing the microorganism-containing bacteria liquid and injecting the microorganism-containing bacteria liquid into the pressure-resistant visual sorting cabin 2 via the microflow pump 11.

More specifically, the pressure-resistant visual sorting cabin 2 further includes a pressure-resistant visual cavity, an annular wall refrigerating/heating cavity 22, and an annular wall high-pressure cavity. The pressure-resistant visual cavity is made of pressure-resistant and anti-corrosion metal material, pressure-resistant visual material is inlaid on a front side and a back side of the pressure-resistant visual cavity, and the whole pressure-resistant visual cavity may bear pressure at a water depth of 5000 meters, and is connected to the pressurization system 4. The carrier chip 21 is disposed in a center of the pressure-resistant visual cavity. An inlet of the microfluidic channel of the carrier chip 21 is connected to the enriched microorganism injection system 1, and an outlet of the microfluidic channel is the outlet end of the pressure-resistant visual sorting cabin 2, and is connected to the automatic sorting system 7. The annular wall high-pressure cavity is disposed at an outer ring of the pressure-resistant visual cavity for protecting the carrier chip 21 against damage in the pressure-resistant visual cavity. The annular wall high-pressure cavity is connected to the pressurization system 4 and the annular pressure controlling system 5. The annular wall refrigerating/heating cavity 22 is wrapped on an outer wall of the pressure-resistant visual cavity to be filled with a refrigerating/heating fluid, and is connected to the annular wall temperature controlling system 3 through the refrigerating/heating fluid.

In a specific implementation process, the pressure-resistant visual cavity is provided with a discharge valve 23, and an output end of the discharge valve is electrically connected to the data acquisition and processing system 8 to facilitate pressure regulation in the cavity. In order to protect the carrier chip 21 against damage in the pressure-resistant visual cavity, the pressure-resistant visual cavity is provided with the annular wall high-pressure cavity for pressurization at the outer ring of the pressure-resistant visual cavity at the same time. In addition, the annular pressure controlling system 5 is provided to automatically increase or decrease pressure of the annular wall high-pressure cavity according to a pressure change of the pressure-resistant visual cavity, so as to achieve pressure balance between the pressure-resistant visual cavity and the annular wall high-pressure cavity and ensure that the carrier chip 21 is subjected to the minimum pressure difference without damage.

In a specific implementation process, the annular wall temperature controlling system 3 adopts a circulating refrigerating/heating device 31 and a temperature sensor 32. A control end of the circulating refrigerating/heating device 31 is electrically connected to the data acquisition and processing system 8 for refrigerating/heating and enabling the refrigerating/heating fluid in the annular wall refrigerating/heating cavity 22 to flow circularly. A probe of the temperature sensor 32 is disposed in the pressure-resistant visual cavity, and a signal output end of the temperature sensor is electrically connected to the data acquisition and processing system 8.

In a specific implementation process, the temperature of the pressure-resistant visual cavity is ensured mainly by injecting the refrigerating/heating fluid in the annular wall refrigerating/heating cavity 22, a low or high temperature state of the fluid in the annular wall refrigerating/heating cavity 22 is ensured by refrigerating or heating the fluid circularly, and a low or high temperature state in the pressure-resistant visual cavity is ensured through heat exchange between the refrigerating/heating fluid and the pressure-resistant visual cavity.

More specifically, the pressurization system 4 includes an air compressor 41, a booster pump 42, a gas storage tank 43, a pressure regulating valve 44, and a pressure sensor 45. The air compressor 41, the booster pump 42, the gas storage tank 43, and the pressure regulating valve 44 are connected in sequence, and then are connected to the pressure-resistant visual cavity and the annular wall high-pressure cavity, respectively. A probe of the pressure sensor 45 is disposed in the pressure-resistant visual cavity, and a signal output end of the pressure sensor is electrically connected to the data acquisition and processing system 8.

In a specific implementation process, the temperature sensor 32 and the pressure sensor 45 are provided to measure and monitor the temperature and pressure of the pressure-resistant visual cavity in the whole microorganism sorting process.

More specifically, the annular pressure controlling system 5 includes an annular pressure detection device 51, a first back pressure tracking pump 52, a back pressure detection device 53, a back pressure valve 54, a buffer tank 55, and a second back pressure tracking pump 56. A probe of the annular pressure detection device 51 is disposed in the annular wall high-pressure cavity, and an output end of the annular pressure detection device is electrically connected to the data acquisition and processing system 8. The first back pressure tracking pump is connected to the annular wall high-pressure cavity, and a control end of the first back pressure tracking pump is electrically connected to the data acquisition and processing system 8. A detection end of the back pressure detection device 53 is connected to the pressure-resistant visual cavity, and a signal output end of the back pressure detection device is electrically connected to the data acquisition and processing system 8. One end of the back pressure valve 54 is connected to the automatic sorting system 7, and the other end of the back pressure valve is connected to the second back pressure tracking pump 56 through the buffer tank 55. A control end of the second back pressure tracking pump 56 is electrically connected to the data acquisition and processing system 8.

More specifically, the optical identification system 6 adopts a spectral/optical observation module, observes and identifies the microorganisms via the spectral/optical observation module when the enriched microorganisms pass through the carrier chip 21, and sends the identification result to the data acquisition and processing system 8.

In the process that the enriched microorganisms pass through the carrier chip 21, the microorganisms are observed and identified via the spectral/optical observation module. The morphology of single cells may be identified by looking over the chip with a high resolution optical microscope, marker biological compounds in the cells may be identified by Raman spectroscopy, and whether microorganisms in the chip are target microorganisms needed by researchers may be determined in combination with optical and spectroscopy identification signals.

More specifically, the automatic sorting system 7 includes an intelligent control tee module 71, a target microorganism storage module 72 and a non-target microorganism storage module 73. The target microorganism storage module 72 and the non-target microorganism storage module 73 are connected to two connecting ends of the intelligent control tee module 71 respectively. Another connecting end of the intelligent control tee module 71 is connected to the outlet end of the pressure-resistant visual sorting cabin 2. A control end of the intelligent control tee module 71 is electrically connected to the data acquisition and processing system 8.

In a specific implementation process, the automatic sorting system 7 is provided at the outlet end of the pressure-resistant visual cavity to perform targeted sorting on the identified microorganisms. The automatic sorting system 7 is mainly controlled by the intelligent control tee module 71. The intelligent control tee module 71 is an automatic opening and closing tee. When it is determined that identified single cells are target microorganisms, a valve of a channel of the target microorganism storage module 72 is opened, and the single cells enter the target microorganism storage module 72. When it is determined that identified single cells are non-target microorganisms, a channel of the non-target microorganism storage module 73 is opened, and the cells enter the non-target microorganism storage module 73. Thus, the purpose of high-throughput single-cell sorting is achieved. The target microorganism storage module 72 may be an atmospheric pressure container or a high pressure container selectively according to experimental needs. The container contains a corresponding culture medium to meet the need that microorganisms continue to be cultured after being sorted.

Example 2

Figure 3:
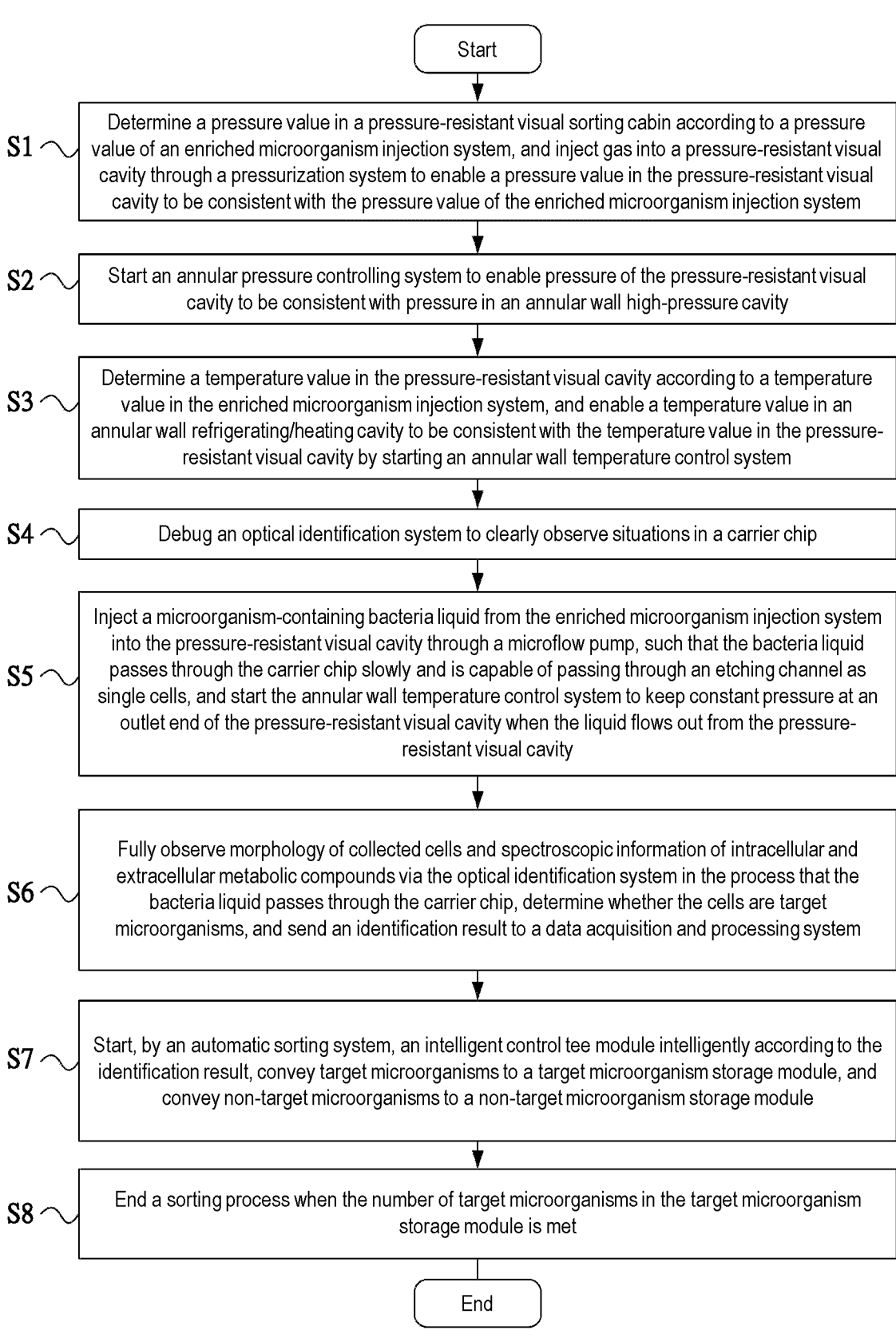
FIG. 3 is a schematic flowchart of a method according to the present invention.

More specifically, as shown in FIG. 3, this solution further provides a method for single-cell high-throughput sorting in a marine in-situ environment. The method is implemented by adopting a device for single-cell high-throughput sorting in the marine in-situ environment, and specifically includes the following steps:

S1: determine a pressure value in a pressure-resistant visual sorting cabin 2 according to a pressure value of an enriched microorganism injection system 1, and inject gas into a pressure-resistant visual cavity through a pressurization system 4 to enable a pressure value in the pressure-resistant visual cavity to be consistent with the pressure value of the enriched microorganism injection system 1;

S2: start an annular pressure controlling system 5 to enable pressure of the pressure-resistant visual cavity to be consistent with pressure in an annular wall high-pressure cavity;

S3: determine a temperature value in the pressure-resistant visual cavity according to a temperature value in the enriched microorganism injection system 1, and enable a temperature value in an annular wall refrigerating/heating cavity 22 to be consistent with the temperature value in the pressure-resistant visual cavity by starting an annular wall temperature controlling system 3;

S4: debug an optical identification system 6 to clearly observe situations in a carrier chip 21;

S5: inject a microorganism-containing bacteria liquid from the enriched microorganism injection system 1 into the pressure-resistant visual cavity through a microflow pump 11, enable the bacteria liquid to pass through the carrier chip 21 slowly so as to allow the bacteria liquid to pass through an etching channel as single cells; and start the annular wall temperature controlling system 3 to keep constant pressure at an outlet end of the pressure-resistant visual cavity when the liquid flows out from the pressure-resistant visual cavity;

S6: fully observe morphology of collected cells and spectroscopic information of intracellular and extracellular metabolic compounds via the optical identification system 6 in the process that the bacteria liquid passes through the carrier chip 21, determine whether the cells are target microorganisms, and send an identification result to a data acquisition and processing system 8;

S7: intelligently start, by an automatic sorting system 7, an intelligent control tee module 71 according to the identification result, convey target microorganisms to a target microorganism storage module 72, and convey non-target microorganisms to a non-target microorganism storage module 73; and S8: end a sorting process when the number of target microorganisms in the target microorganism storage module 72 is met.

More specifically, before step S1 is carried out, pretreatment needs to be carried out on the device for single-cell high-throughput sorting in the marine in-situ environment as follows: open the outlet end of the pressure-resistant visual cavity, and repeatedly clean the pressure-resistant visual cavity by pumping in deionized water; after thorough rinsing, pump in 75% alcohol; and after the pressure-resistant visual cavity is completely filled with alcohol, close the pressure-resistant visual cavity, perform standing for 24 hours, and then discharge the alcohol in the pressure-resistant visual cavity to complete the pretreatment.

In the whole sorting process, the pressure and temperature values in the pressure-resistant visual cavity are kept consistent with the pressure and temperature environment in the enriched microorganism injection system 1 where the microorganisms are initially located, such that the microorganisms are sorted under in-situ high-pressure conditions. In the sorting process, the annular pressure controlling system 5 is started to keep the pressure value in the annular wall high-pressure cavity consistent with that in the pressure-resistant visual cavity according to a pressure value change therein, such that the carrier chip 21 is not subjected to a pressure difference and is prevented from being deformed and damaged.

Through chips and technology for high-throughput single-cell sorting of marine microorganisms in the high-pressure environment provided in this example, identification and sorting of microorganisms in the marine high-pressure environment can be achieved, and the requirements of subsequent pure culture can be met. Compared with current traditional technology for enrichment and isolation of marine microorganisms in an atmospheric pressure environment, the problems that marine pressure-resistant bacteria and barophilic bacteria have a low survival rate in the atmospheric pressure environment, and deep-sea indigenous characteristics cannot be effectively expressed in the atmospheric pressure environment can be effectively solved, and the problems of low culture degree of marine microorganisms and difficulty in culturing pure bacteria at present are solved. Meanwhile, this solution can realize high-throughput identification and automatic sorting at single-cell scale in the high-pressure environment, which effectively improves the efficiency of microorganism culture and purification compared with conventional microorganism isolation and culture technology.

Example 3

More specifically, in order to further illustrate the technical implementation process and technical effects of this solution, a microfluidic chip for high-throughput single-cell sorting of deep-sea methanotrophs in a high-pressure environment involved in this example can realize high-throughput single-cell sorting of enriched deep-sea methanotrophs in an in-situ high-pressure environment, and meet requirements of subsequent work such as culture and functional identification. The core of this example is a high-pressure resistant and visual pressure-resistant visual sorting cabin 2. Other parts mainly include a pressurization system 4, an annular pressure controlling system 5, an optical identification system 6, an automatic sorting system 7, and a data acquisition and processing system 8.

The pressure-resistant visual sorting cabin 2, as the core component, mainly includes a pressure-resistant visual cavity, a carrier chip 21, an annular wall refrigerating/heating cavity 22, and an annular wall high-pressure cavity. The pressure-resistant visual cavity is made of pressure-resistant and anti-corrosion titanium alloy material, a front side and a back side of a cavity body are inlaid with pressure-resistant visual sapphire material, and the whole pressure-resistant visual cavity may withstand pressure at a water depth of 5000 meters. The carrier chip 21 is disposed in the center of the pressure-resistant visual cavity, and the carrier chip 21 is provided with a microfluidic channel. A microorganism-containing bacteria liquid is injected from a high-pressure microorganism enrichment and culturing chamber 12 into the pressure-resistant visual cavity through a microflow pump 11, the bacteria liquid passes through the carrier chip 21 slowly, and methane is injected from the pressurization system 4. An inlet pressure detection device 13 is disposed between the enriched microorganism injection system 1 and the pressure-resistant visual sorting cabin 2. An outlet end of the pressure-resistant visual cavity is mainly used for a sorted fluid containing a deep-sea methanotroph enrichment solution to leave the pressure-resistant visual cavity and enter the automatic sorting system 7. The annular pressure controlling system 5 is disposed at the outlet end for back pressure control, and mainly includes a back pressure detection device 53, a back pressure valve 54, a buffer tank 55, and a second back pressure tracking pump 56. It is ensured that the microorganism-containing fluid flows out from the sorting system under set pressure conditions, and the pressure in the pressure-resistant visual cavity is kept constant in the whole sorting process. The pressure-resistant visual cavity is provided with a discharge valve 23 to facilitate pressure regulation in the cavity. The pressure-resistant visual cavity is provided with a temperature sensor 32 and a pressure sensor 45 to measure and monitor the temperature and pressure in the cavity in the sorting process of deep-sea methanotrophs. The carrier chip 21 is made of visual material and embedded with the etching microfluidic channel, such that the enriched deep-sea methanotroph can pass through the chip at a small flow rate after entering the pressure-resistant visual sorting cabin, and dispersed passage of single cells are dispersed and pass through the channel. In order to protect the carrier chip 21 against damage in the pressure-resistant visual cavity, the pressure-resistant visual cavity is provided with the annular wall high-pressure cavity for pressurization at an outer ring of the pressure-resistant visual cavity at the same time. In addition, the annular pressure controlling system 5 is provided to automatically increase or decrease pressure of the annular wall high-pressure cavity according to a pressure change of the pressure-resistant visual cavity, so as to achieve pressure balance between the pressure-resistant visual cavity and the annular wall high-pressure cavity and ensure that the carrier chip 21 is subjected to the minimum pressure difference without damage. The temperature of the pressure-resistant visual cavity is ensured mainly by injecting refrigerating/ heating fluid, such as a glycol-containing refrigeration solution, in the annular wall refrigerating/heating cavity 22, the fluid in the annular wall refrigerating/heating cavity is kept at a low temperature of 4° C. by refrigerating/heating the fluid circularly, and a low-temperature state in the pressure-resistant visual cavity is ensured through heat exchange between the refrigerating fluid and the pressure-resistant visual cavity.

In the process that the enriched microorganisms pass through the sorting chip, microorganisms are observed and identified through a spectral/optical observation module. For example, the morphology of single cells may be identified by looking over the chip with a high resolution optical microscope, marker biological compounds in the cells may be identified by Raman spectroscopy, and whether microorganisms in the chip are deep-sea methanotrophs may be determined in combination with optical and spectroscopy identification signals. The automatic sorting system 7 is provided at the outlet of the pressure-resistant visual cavity to perform targeted sorting on the identified microorganisms. The automatic sorting system is provided with an intelligent control tee module 71. The intelligent control tee module 71 is an automatic opening and closing tee. When it is determined that identified single cells are deep-sea methanotrophs, a valve of a channel of a target microorganism storage module 72 is opened, and the single cells enter the target microorganism storage module 72. When it is determined that identified single cells are not deep-sea methanotrophs, a collection channel of a non-target microorganism storage module 73 is opened, and the cells enter the non-target microorganism storage module 73. Thus, the purpose of high-throughput single-cell sorting is achieved. The target microorganism storage module 72 may be an atmospheric pressure container or a high pressure container to meet the need that deep-sea methanotrophs continue to be cultured in the high-pressure environment after being sorted.

The technology for high-throughput single-cell sorting of marine microorganisms in the high-pressure environment involved in this example is mainly required to build the same high-pressure environment as a deep-sea environment where deep-sea methanotrophs live in the pressure-resistant visual cavity. Firstly, the pressure-resistant visual cavity is cleaned, an inlet and an outlet are opened, deionized water is pumped in for repeated rinsing, 75% alcohol is pumped in after thorough rinsing, the pressure-resistant visual cavity is closed after being completely filled with alcohol, standing is performed for 24 hours, and the alcohol is discharged. Then, the pressure value in the pressure-resistant visual cavity is determined according to an initial pressure value of 12 MPa in the enriched microorganism injection system 1, and $CH_4$ gas is injected into the pressure-resistant visual cavity through the pressurization system 4 to increase the pressure in the pressure-resistant visual cavity to 12 MPa. The annular pressure controlling system 5 is started to enable the pressure value in the annular wall high-pressure cavity to be consistent with the pressure in the pressure-resistant visual cavity. In the sorting process, if the pressure in the pressure-resistant visual cavity changes, the pressure in the annular wall high-pressure cavity is made to be consistent with the pressure in the pressure-resistant visual cavity by injecting gas into the annular wall high-pressure cavity through a first back pressure tracking pump 52 or opening a valve for pressure relief. Then, a temperature value in the pressure-resistant visual cavity is determined according to a temperature value of 4° C. in the enriched microorganism injection system 1, and a temperature value in the annular wall refrigerating/heating cavity is made to be consistent with the temperature in the pressure-resistant visual cavity by starting an annular wall temperature controlling system 3. Then, a spectral/optical observation module is debugged to clear observe conditions in the carrier chip 21. Then, a bacteria liquid containing deep-sea methanotrophs is injected from the enriched microorganism injection system 1 into the pressure-resistant visual cavity via the microflow pump 11, the outlet is opened for back pressure, and the outlet pressure is set as 11.5 MPa. The bacteria liquid passes through the carrier chip 21 slowly so as to pass through the etching channel as single cells. In the process that the bacteria liquid passes through the carrier chip 21, the spectral/optical observation module is started to fully observe the morphology of collected cells and spectroscopic information of single-cell microorganisms, and determine whether the cells are methanotrophs. If the cells are methanotrophs, a valve of the automatic sorting system 7 is opened to allow the cells to enter a methanotroph collection module. If the cells are not methanotrophs, the cells enter a non-target bacteria collection module. When all fluids in the enriched microorganism injection system 1 are sorted and identified, the sorting process is ended. In the whole sorting process, the pressure and temperature values in the pressure-resistant visual cavity are kept consistent with the pressure and temperature environment in the enriched microorganism injection system 1 where the deep-sea methanotrophs are initially located, such that the microorganisms are sorted under in-situ high-pressure conditions. In the sorting process, the annular pressure controlling system 5 is started to keep the pressure value in the annular wall high-pressure cavity consistent with that in the pressure-resistant visual cavity according to a pressure value change therein, such that the carrier chip 21 is not subjected to a pressure difference and is prevented from being deformed and damaged.

It is apparent that the above embodiments of the present invention are merely examples of the present invention for purposes of clarity and are not intended to limit the implementations of the present invention. Changes or modifications in other different forms can also be made by those of ordinary skill in the art on the basis of the above description. All implementations need not to be, and cannot be, exhaustive. Any modifications, equivalent replacements, improvements, etc. made within the spirit and principle of the present invention shall fall within the protection scope of the claims of the present invention.

What is claimed is:

1. A device for single-cell high-throughput sorting in a marine in-situ environment, comprising an enriched microorganism injection system, a pressure-resistant visual sorting cabin, an annular wall temperature controlling system, a pressurization system, an annular pressure controlling system, an optical identification system, an automatic sorting system, and a data acquisition and processing system, wherein the enriched microorganism injection system is used for culturing and injecting a microorganism-containing bacteria liquid into the pressure-resistant visual sorting cabin;

a carrier chip is disposed in the pressure-resistant visual sorting cabin, the carrier chip is made of visual material and embedded with an etching microfluidic channel for allowing the enriched microorganisms to be dispersed and to pass through the channel; when the enriched microorganisms pass through the carrier chip, the microorganisms are observed and identified via the optical identification system;

an outlet end of the pressure-resistant visual sorting cabin is connected to the automatic sorting system, and the automatic sorting system automatically sorts the microorganisms according to a microorganism identification result of the optical identification system;

the annular wall temperature controlling system is used for ensuring consistent internal temperature of the pressure-resistant visual sorting cabin;

the pressurization system is used for enabling internal pressure of the pressure-resistant visual sorting cabin to be consistent with internal pressure of the enriched microorganism injection system;

the annular pressure controlling system is used for keeping the internal pressure of the pressure-resistant visual sorting cabin consistent with internal pressure of the automatic sorting system according to a pressure value change therein, so as to avoid deformation or damage to the carrier chip from a pressure difference; and the enriched microorganism injection system, the annular wall temperature controlling system, the pressurization system, the annular pressure controlling system, the optical identification system, and the automatic sorting system are all electrically connected to the data acquisition and processing system, wherein the pressure-resistant visual sorting cabin further comprises a pressure-resistant visual cavity, an annular wall refrigerating/heating cavity, and an annular wall high-pressure cavity;

the pressure-resistant visual cavity is made of pressure-resistant and anti-corrosion metal material, pressure-resistant visual material is inlaid on a front side and a back side of the pressure-resistant visual cavity, and the pressure-resistant visual cavity is connected to the pressurization system;

the carrier chip is disposed in a center of the pressure-resistant visual cavity; an inlet of the microfluidic channel of the carrier chip is connected to the enriched microorganism injection system, and an outlet of the microfluidic channel is the outlet end of the pressure-resistant visual sorting cabin, and is connected to the automatic sorting system;

the annular wall high-pressure cavity is disposed at an outer ring of the pressure-resistant visual cavity for protecting the carrier chip against damage in the pressure-resistant visual cavity; the annular wall high-pressure cavity is connected to the pressurization system and the annular pressure controlling system; and the annular wall refrigerating/heating cavity is wrapped on an outer wall of the pressure-resistant visual cavity for loading a refrigerating/heating fluid, and is connected to the annular wall temperature controlling system through the refrigerating/heating fluid.

2. The device for single-cell high-throughput sorting in a marine in-situ environment according to claim 1, wherein the enriched microorganism injection system comprises a microflow pump, a high-pressure microorganism enrichment and culturing chamber and an inlet pressure detection device;

a control end of the microflow pump is electrically connected to the data acquisition and processing system;

an input end of the microflow pump is connected to a liquid outlet end of the high-pressure microorganism enrichment and culturing chamber, and an output end of the microflow pump is connected to an inlet end of the pressure-resistant visual sorting cabin through the inlet pressure detection device; and the high-pressure microorganism enrichment and culturing chamber is used for culturing the microorganism-containing bacteria liquid and injecting the microorganism-containing bacteria liquid into the pressure-resistant visual sorting cabin via the microflow pump.

3. A method for single-cell high-throughput sorting in a marine in-situ environment, being implemented by adopting the device for single-cell high-throughput sorting in the marine in-situ environment according to claim 2, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

4. The method for single-cell high-throughput sorting in a marine in-situ environment according to claim 3, wherein before step S1 is carried out, pretreatment needs to be carried out on the device for single-cell high-throughput sorting in the marine in-situ environment as follows:

opening the outlet end of the pressure-resistant visual cavity, and repeatedly cleaning the pressure-resistant visual cavity by pumping in deionized water; after thorough rinsing, pumping in 75% alcohol; and after the pressure-resistant visual cavity is completely filled with alcohol, closing the pressure-resistant visual cavity, performing standing for 24 hours, and then discharging the alcohol in the pressure-resistant visual cavity to complete the pretreatment.

5. The device for single-cell high-throughput sorting in a marine in-situ environment according to claim 1, wherein the annular wall temperature controlling system adopts a circulating refrigerating/heating device and a temperature sensor; a control end of the circulating refrigerating/heating device is electrically connected to the data acquisition and processing system for refrigerating/heating and enabling the refrigerating/heating fluid in the annular wall refrigerating/heating cavity to flow circularly; and a probe of the temperature sensor is disposed in the pressure-resistant visual cavity, and a signal output end of the temperature sensor is electrically connected to the data acquisition and processing system.

6. A method for single-cell high-throughput sorting in a marine in-situ environment, being implemented by adopting the device for single-cell high-throughput sorting in the marine in-situ environment according to claim 5, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

7. The method for single-cell high-throughput sorting in a marine in-situ environment according to claim 6, wherein before step S1 is carried out, pretreatment needs to be carried out on the device for single-cell high-throughput sorting in the marine in-situ environment as follows:

opening the outlet end of the pressure-resistant visual cavity, and repeatedly cleaning the pressure-resistant visual cavity by pumping in deionized water; after thorough rinsing, pumping in 75% alcohol; and after the pressure-resistant visual cavity is completely filled with alcohol, closing the pressure-resistant visual cavity, performing standing for 24 hours, and then discharging the alcohol in the pressure-resistant visual cavity to complete the pretreatment.

8. The device for single-cell high-throughput sorting in a marine in-situ environment according to claim 1, wherein the pressurization system comprises an air compressor, a booster pump, a gas storage tank, a pressure regulating valve, and a pressure sensor; the air compressor, the booster pump, the gas storage tank, and the pressure regulating valve are connected in sequence, and then are connected to the pressure-resistant visual cavity and the annular wall high-pressure cavity, respectively; and a probe of the pressure sensor is disposed in the pressure-resistant visual cavity, and a signal output end of the pressure sensor is electrically connected to the data acquisition and processing system.

9. A method for single-cell high-throughput sorting in a marine in-situ environment, being implemented by adopting the device for single-cell high-throughput sorting in the marine in-situ environment according to claim 8, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

10. The device for single-cell high-throughput sorting in a marine in-situ environment according to claim 1, wherein the annular pressure controlling system comprises an annular pressure detection device, a first back pressure tracking pump, a back pressure detection device, a back pressure valve, a buffer tank, and a second back pressure tracking pump; wherein a probe of the annular pressure detection device is disposed in the annular wall high-pressure cavity, and an output end of the annular pressure detection device is electrically connected to the data acquisition and processing system; the first back pressure tracking pump is connected to the annular wall high-pressure cavity, and a control end of the first back pressure tracking pump is electrically connected to the data acquisition and processing system;

a detection end of the back pressure detection device is connected to the pressure-resistant visual cavity, and a signal output end of the back pressure detection device is electrically connected to the data acquisition and processing system;

one end of the back pressure valve is connected to the automatic sorting system, and the other end of the back pressure valve is connected to the second back pressure tracking pump through the buffer tank; and a control end of the second back pressure tracking pump is electrically connected to the data acquisition and processing system.

11. A method for single-cell high-throughput sorting in a marine in-situ environment, being implemented by adopting the device for single-cell high-throughput sorting in the marine in-situ environment according to claim 10, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

12. The device for single-cell high-throughput sorting in a marine in-situ environment according to claim 1, wherein the optical identification system adopts a spectral/optical observation module, observes and identifies the microorganisms via the spectral/optical observation module when the enriched microorganisms pass through the carrier chip, and sends the identification result to the data acquisition and processing system.

13. A method for single-cell high-throughput sorting in a marine in-situ environment, being implemented by adopting the device for single-cell high-throughput sorting in the marine in-situ environment according to claim 12, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

14. The device for single-cell high-throughput sorting in a marine in-situ environment according to claim 1, wherein the automatic sorting system comprises an intelligent control tee module, a target microorganism storage module and a non-target microorganism storage module; the target microorganism storage module and the non-target microorganism storage module are connected to two connecting ends of the intelligent control tee module respectively, and another connecting end of the intelligent control tee module is connected to the outlet end of the pressure-resistant visual sorting cabin; and a control end of the intelligent control tee module is electrically connected to the data acquisition and processing system.

15. A method for single-cell high-throughput sorting in a marine in-situ environment, being implemented by adopting the device for single-cell high-throughput sorting in the marine in-situ environment according to claim 14, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

16. A method for single-cell high-throughput sorting in a marine in-situ environment, being implemented by adopting the device for single-cell high-throughput sorting in the marine in-situ environment according to claim 1, and specifically comprising the following steps:

S1: determining a pressure value in a pressure-resistant visual sorting cabin according to a pressure value of an enriched microorganism injection system, and injecting gas into a pressure-resistant visual cavity through a pressurization system to enable a pressure value in the pressure-resistant visual cavity to be consistent with or have a small difference from the pressure value of the enriched microorganism injection system;

S2: starting an annular pressure controlling system to enable pressure of the pressure-resistant visual cavity to be consistent with pressure in an annular wall high-pressure cavity;

S3: determining a temperature value in the pressure-resistant visual cavity according to a temperature value in the enriched microorganism injection system, and enabling a temperature value in an annular wall refrigerating/heating cavity to be consistent with the temperature value in the pressure-resistant visual cavity by starting an annular wall temperature controlling system;

S4: debugging an optical identification system to clearly observe situations in a carrier chip;

S5: injecting a microorganism-containing bacteria liquid from the enriched microorganism injection system into the pressure-resistant visual cavity through a microflow pump, enabling the bacteria liquid to pass through the carrier chip slowly so as to allow the bacteria liquid to pass through an etching channel as single cells; and starting the annular wall temperature controlling system to keep constant pressure at an outlet end of the pressure-resistant visual cavity when the liquid flows out from the pressure-resistant visual cavity;

S6: fully observing morphology of collected cells and spectroscopic information of single-cell microorganisms via the optical identification system in the process that the bacteria liquid passes through the carrier chip, determining whether the cells are target microorganisms, and sending an identification result to a data acquisition and processing system;

S7: intelligently starting, by an automatic sorting system, an intelligent control tee module according to the identification result, conveying target microorganisms to a target microorganism storage module, and conveying non-target microorganisms to a non-target microorganism storage module; and S8: ending a sorting process when the number of target microorganisms in the target microorganism storage module is met.

17. The method for single-cell high-throughput sorting in a marine in-situ environment according to claim 16, wherein before step S1 is carried out, pretreatment needs to be carried out on the device for single-cell high-throughput sorting in the marine in-situ environment as follows:

opening the outlet end of the pressure-resistant visual cavity, and repeatedly cleaning the pressure-resistant visual cavity by pumping in deionized water; after thorough rinsing, pumping in 75% alcohol; and after the pressure-resistant visual cavity is completely filled with alcohol, closing the pressure-resistant visual cavity, performing standing for 24 hours, and then discharging the alcohol in the pressure-resistant visual cavity to complete the pretreatment.

* * * * *